(12) United States Patent
Sheng et al.

(10) Patent No.: US 9,708,301 B2
(45) Date of Patent: Jul. 18, 2017

(54) CRYSTALLINE FORMS OF AFATINIB MONOMALEATE, PREPARATION METHODS AND PHARMACEUTICAL COMPOSITIONS THEREOF

(71) Applicant: Hangzhou Pushai Pharmaceutical Technology Co., LTD., Hangzhou (CN)

(72) Inventors: Xiaohong Sheng, Hangzhou (CN); Jianfeng Zheng, Hangzhou (CN); Xiaoxia Sheng, Hangzhou (CN)

(73) Assignee: HANGZHOU PUSHAI PHARMACEUTICAL TECHNOLOGY, Hangzhou (CN)

( * ) Notice: Subject to any disclaimer, the term of this patent is extended or adjusted under 35 U.S.C. 154(b) by 23 days.

(21) Appl. No.: 14/995,605

(22) Filed: Jan. 14, 2016

(65) Prior Publication Data
US 2016/0207907 A1 Jul. 21, 2016

(30) Foreign Application Priority Data

Jan. 15, 2015 (CN) .......................... 2015 1 0020869

(51) Int. Cl.
*A61K 31/517* (2006.01)
*C07D 405/12* (2006.01)
*C07C 57/145* (2006.01)

(52) U.S. Cl.
CPC .......... *C07D 405/12* (2013.01); *C07C 57/145* (2013.01)

(58) Field of Classification Search
CPC ........................... C07D 405/12; C07C 57/145
See application file for complete search history.

(56) References Cited

U.S. PATENT DOCUMENTS

| 7,019,012 B2 | 3/2006 | Himmelsbach et al. |
| 8,426,586 B2 | 4/2013 | Soyka et al. |
| 2005/0085495 A1* | 4/2005 | Soyka .................. C07D 405/12 514/266.24 |

FOREIGN PATENT DOCUMENTS

| CN | 1867564 A | 11/2006 |
| WO | WO 02/50043 A1 | 6/2002 |
| WO | WO 2005/037824 A2 | 4/2005 |
| WO | WO 2007/054550 A1 | 5/2007 |
| WO | WO 2007/054551 A1 | 5/2007 |
| WO | WO 2009/147238 A1 | 12/2009 |
| WO | WO 2012/121764 A1 | 9/2012 |
| WO | WO 2013/052157 A1 | 4/2013 |

* cited by examiner

*Primary Examiner* — Jason Sims
*Assistant Examiner* — Ibrahim D Bori
(74) *Attorney, Agent, or Firm* — Sterne, Kessler, Goldstein & Fox PLLC

(57) ABSTRACT

The present invention relates to the novel solid forms of Afatinib monomaleate and preparation methods thereof; the solid forms of Afatinib monomaleate of the present invention have many improved properties as compared to the known crystalline form of Afatinib salt; and the present invention also relates to pharmaceutical compositions containing the novel solid forms of Afatinib monomaleate as well as the uses thereof for treating terminal non-small cell lung cancer (NSCLS) and HER2 positive advanced breast cancer.

12 Claims, 4 Drawing Sheets

CRYSTALLINE FORMS OF AFATINIB MONOMALEATE, PREPARATION METHODS AND PHARMACEUTICAL COMPOSITIONS THEREOF

BACKGROUND OF THE INVENTION

Field of the Invention

The present invention relates to the technical field of crystallization in pharmaceutical chemistry. Specifically, the present invention relates to novel solid forms of Afatinib monomaleate and preparation methods, pharmaceutical compositions and uses thereof.

Background

The chemical name of Afatinib is N-[4-(3-chloro-4-fluorophenyl)amino]-7-[[(3S)-tetrahydro-3-furanyl]oxy]-6-quinazolinyl]-4-(dimethylamino)-2-butenamide. It is also called BIBW 2992. The molecular formula is $C_{24}H_{25}ClFN_5O_3$ and the chemical structural formula is shown below:

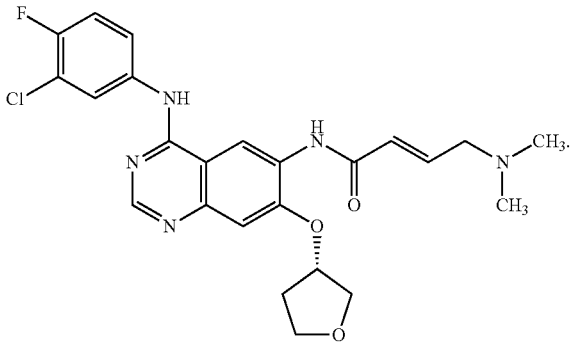 [SMILES: CN(C)C/C=C/C(=O)Nc1cc2c(Nc3ccc(F)c(Cl)c3)ncnc2cc1O[C@H]1CCOC1]

Afatinib was developed by Boehringer Ingelheim Pharmaceuticals, Inc. Afatinib was approved by U.S. Food and Drug Administration and the European Medicines Agency in 2013, used in treating patients with EGFR mutated terminal or metastatic non-small cell lung cancer (NSCLC). The approved dosages are oral tablets. Afatinib is a powerful and selective dual irreversible epidermal growth factor receptor (EGFR) and human epidermal growth factor receptor-2 (HER2) tyrosine kinases inhibitor.

Patent document WO2002/50043A1 disclosed the compound of Afatinib. Patent documents WO2007/054550A1 and WO2007/054551A1 disclosed indications of Afatinib.

Patent document WO2005/037824A2 (corresponding to patent document CN1867564B) disclosed a preparation method of crystalline form of Afatinib dimaleate. For convenience purpose, in the present invention, the Afatinib dimaleate described in WO2005/037824A2 is designated as "the crystalline form of Afatinib dimaleate in the prior art"

Patent document WO2009/147238A1 disclosed that Afatinib dimaleate described in WO2005/037824A2 has a fine needle-like morphology, which may lead to problems such as significant variations in bulk density and flowability issues due to orientation of needle-like particles, also may lead to capping or stacking, poor compressibility and API surface adhesion caused by increased electrostatic charge during the direct-compression processes of the tablets. The present inventors also found the solubility of the crystalline form of Afatinib dimaleate in the prior art is lower.

WO2012/121764A1 disclosed Form B of Afatinib dimaleate.

WO2013/052157A1 disclosed Forms C, D, E of Afatinib dimaleate. The researches by the present inventors showed that the Forms B, C, D, E of Afatinib dimaleate have serious hygroscopicity issues and are not suitable for storage and formulation application.

Patent document WO2012/121764A1 also disclosed various Afatinib acid addition salts and their crystalline forms, for example, Afatinib salts formed by Afatinib free base with one or more $H_mX$ wherein m is natural number, X is an anion of a pharmaceutically acceptable acid such as maleate, fumarate and so on. It also disclosed amorphous form of Afatinib diphenyl sulfonate salt, crystalline form of Afatinib fumarate salt, crystalline form of Afatinib disulphate salt, crystalline form of Afatinib dihydrochloride salt, crystalline form of Afatinib dioxalate salt, crystalline form of Afatinib dimesylate salt, crystalline form of Afatinib diphosphate salt, amorphous form of Afatinib di-L-malate salt, amorphous form of Afatinib citrate salt, crystalline form of Afatinib disuccinate salt, crystalline form of Afatinib di-L-aspartate salt, crystalline form of Afatinib difumarate salt. The patent document only generally mentioned that the above Afatinib acid addition salts and their crystalline forms have at least one beneficial property, but for any one of the above Afatinib acid addition salts or their crystalline forms, the patent document provided neither the kinds of beneficial properties nor test data relating to the beneficial properties and comparative data for practical applications.

Therefore, there is a need of developing Afatinib acid addition salts and their crystalline forms with more superior properties.

SUMMARY OF THE INVENTION

In view of the defects in the prior art, the objective of the present invention is to provide novel crystalline forms or amorphous forms of Afatinib monomaleate with one or more improved properties, and furthermore to provide their preparation methods, pharmaceutical compositions and uses.

According to the objective of the present invention, the present invention provides crystalline form N of Afatinib monomaleate and preparation method thereof.

The structural formula of the crystalline form N of Afatinib monomaleate in the present invention is shown below:

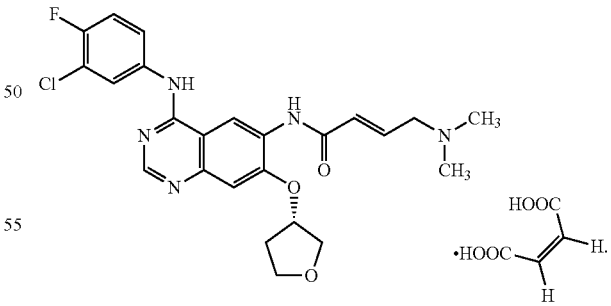

The crystalline form N of Afatinib monomaleate, wherein measured using Cu-Kα radiation, the X-ray powder diffraction pattern of the crystalline Form N of Afatinib monomaleate, expressed as 2θ angles, has the following characteristic peaks: 3.8±0.2°, 5.1±0.2°, 5.8±0.2°, 10.1±0.2°, 14.9±0.2° and 20.2±0.2°.

Preferably, the X-ray powder diffraction pattern of the crystalline Form N of Afatinib monomaleate, expressed as 2θ angles, has the following characteristic peaks: 3.8±0.2°, 5.1±0.2°, 5.8±0.2°, 6.8±0.2°, 8.3±0.2°, 10.1±0.2°, 11.2±0.2°, 14.9±0.2°, 15.7±0.2°, 18.9±0.2°, 20.2±0.2° and 25.0±0.2°.

Further preferably, the X-ray powder diffraction pattern of the crystalline Form N of Afatinib monomaleate, expressed as 2θ angles, has the following characteristic peaks with their relative intensities:

| Diffraction angle 2θ | Relative intensity % |
|---|---|
| 3.8 ± 0.2° | 39.7 |
| 5.1 ± 0.2° | 100.0 |
| 5.8 ± 0.2° | 48.9 |
| 6.8 ± 0.2° | 14.6 |
| 8.3 ± 0.2° | 21.0 |
| 10.1 ± 0.2° | 36.8 |
| 11.2 ± 0.2° | 17.7 |
| 14.9 ± 0.2° | 30.8 |
| 15.7 ± 0.2° | 28.5 |
| 16.1 ± 0.2° | 24.8 |
| 16.5 ± 0.2° | 12.8 |
| 17.8 ± 0.2° | 18.4 |
| 18.9 ± 0.2° | 29.3 |
| 20.2 ± 0.2° | 67.4 |
| 21.2 ± 0.2° | 28.5 |
| 23.1 ± 0.2° | 30.9 |
| 25.0 ± 0.2° | 71.4 |
| 25.5 ± 0.2° | 34.7 |
| 27.2 ± 0.2° | 35.1. |

Non-restrictively, in one specific embodiment, the X-ray powder diffraction pattern of the crystalline Form N of Afatinib monomaleate is substantially similar to FIG. 4.

Polarizing microscope (PLM) image of the crystalline Form N of Afatinib monomaleate shows fine granular crystals.

A preparation method of the crystalline Form N of Afatinib monomaleate, comprising: forming Afatinib free base solution in a soluble solvent; adding maleic acid with its molar amount of 1~1.5 times to Afatinib free base; mixing and forming a solution; adding an anti-solvent to the solution and stirring the solution for crystallization to occur; and separating and drying the precipitated solids to obtain the crystalline Form N of Afatinib monomaleate, wherein the soluble solvent is selected from the group consisting of $C_1$~$C_4$ alcohols, $C_3$~$C_5$ esters and $C_3$~$C_5$ cyclic ethers, and the anti-solvent is selected form $C_4$~$C_6$ non-cyclic ethers and $C_6$~$C_8$ alkanes.

The $C_1$~$C_4$ alcohols include methanol, ethanol, n-propanol, isopropanol, n-butanol, 2-butyl alcohol and tert-butanol; the $C_3$~$C_5$ esters include ethyl acetate, methyl acetate, ethyl formate, isopropyl acetate and propyl acetate; the $C_3$~$C_5$ cyclic ethers include tetrahydrofuran, methyltetrahydrofuran, 1,4-dioxane and 1,3-dioxolane; the $C_4$~$C_6$ non-cyclic ethers include methyl tert-butyl ether, isopropyl ether, propyl ether, ether and ethyl butyl ether; and the $C_6$~$C_8$ alkanes include cyclohexane, methylcyclohexane, hexane, n-heptane and n-octane.

Preferably, the soluble solvent is selected from the group consisting of ethanol, isopropanol, ethyl acetate and tetrahydrofuran, and the anti-solvent is methyl tert-butyl ether or n-heptane.

Preferably, the preparation method is performed at room temperature.

Preferably, the time of crystallization is 1 to 3 days.

Preferably, the concentration of Afatinib free base in the soluble solvent is 50 to 250 mg/mL and the ratio of the soluble solvent to the anti-solvent is 1:1 to 1:5.

According to the objective of the present invention, the present invention provides an amorphous form of Afatinib monomaleate and preparation methods thereof.

The structural formula of the amorphous form of Afatinib monomaleate in the present invention is shown below:

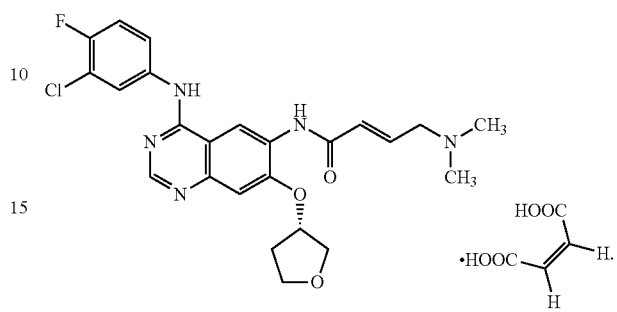

Non-restrictively, measured using Cu-Kα radiation, the X-ray powder diffraction pattern of the amorphous form of Afatinib monomaleate is substantially similar to FIG. 7.

A preparation method of the amorphous form of Afatinib monomaleate, comprising: forming Afatinib free base solution in a soluble solvent; adding maleic acid with its molar amount of 1~1.5 times to Afatinib free base; mixing and forming a solution; concentrating to dryness under reduced pressure; and obtaining the amorphous form of Afatinib monomaleate.

Preferably, the soluble solvent is selected from the group consisting of alcohol, ester, ketone, ether, halogenated alkane and their mixtures.

The specific operations of "concentrate to dryness under reduced pressure" are as follows: place the container of the solution in a rotary evaporation instrument and completely remove the solvent at a water bath temperature between room temperature and the boiling point of the solvent (preferably 30 to 50° C.), under less than atmospheric pressure (preferably less than 0.08 MPa) and the rotational speed of 10 to 180 r/min (preferably 50 to 100 r/min).

Compared to the crystalline form of Afatinib dimaleate salt in the prior art, the crystalline Form N or the amorphous form of Afatinib monomaleate of the present invention shows one or more improved properties, such as higher crystallinity, better solubility and dissolution rate, better crystalline morphology, better thermal stability and storage stability, lower hygroscopicity, higher active ingredient content, better flowability, better dissolution and better processing properties of formulations, easier preparation under the condition of room temperature or lower temperature and is more suitable for commercial production.

Especially, the crystalline Form N of Afatinib monomaleate has the following advantageous properties:
1) The solubility of the crystalline Form N of Afatinib monomaleate in water at room temperature is 126.9 mg/mL, which is higher than that of the crystalline form of Afatinib dimaleate in the prior art under the same conditions (7.5 mg/mL).
2) Being fine granular crystals, the crystalline Form N of Afatinib monomaleate has better flowability compared to the needle-like crystalline form of Afatinib dimaleate in the prior art. There is no sticking phenomenon observed during its tableting process and the obtained tablet has high hardness. It has better compressibility and processibility.

3) The active pharmaceutical ingredient content of Afatinib monomaleate is higher than that of Afatinib dimaleate, which means higher drug loading in formulation application.

The above advantageous properties indicate that, compared to the crystalline form of Afatinib dimaleate in the prior art, the crystalline Form N of Afatinib monomaleate of the present invention has many advantageous characteristics and better application properties, and is suitable to be the active ingredient in pharmaceutical formulations. The better solubility of the active ingredient is beneficial to improve dissolution and bioavailability of the drug and have a positive effect on drug efficacy. The active ingredient with good crystal morphology has better flowability, better compressibility and better processibility, as well as good adaptability in formulation process.

In the above preparation methods of the crystalline Form N and the amorphous form of Afatinib monomaleate of the present invention: the mentioned "mix" or "stir" may be performed by routine technology, such as magnetic stirring and mechanical stirring. The stirring speed is 50~1800 r/min, preferably 300~900 r/min.

In the preparation methods of the crystalline Form N of Afatinib monomaleate of the present invention: the mentioned "separate" may be performed by routine methods in the field such as filtration and centrifugation. The detailed operation of filtration is: place the sample to be separated on filter paper and filter it under reduced pressure. The detailed operation of centrifugation is: place the sample to be separated in a centrifuge tube, spin at a high speed until the solids completely settle down at the bottom of the tube. The centrifugation speed is, for example, 6000 r/min.

In the preparation methods of the crystalline Form N of Afatinib monomaleate of the present invention: the mentioned "dry" may be performed by routine methods in the field such as forced air drying and drying under reduced pressure (vacuum drying). Preferably, drying under a reduced pressure of less than 0.09 MPa. The drying temperature is room temperature to 50° C., the drying time is 10-72 hours, preferably 8-24 hours. Drying may be performed in fume hood, forced air oven or vacuum oven.

Terms used in the present invention are explained below:
The room temperature refers to 10 to 30° C.
The time of overnight is 8 to 16 hours.
Sonication helps dissolving a sample and the detailed operations are as follows: place the container of the solution or suspension in an ultrasonic cleaner and sonicate at a power of 20 to 40 Khz. Generally, the sample is sonicated at 40 Khz for 5 minutes.

According to the objective of the present invention, the present invention provides a pharmaceutical composition, which comprises a therapeutically effective amount of active pharmaceutical ingredient selected from the crystalline Form N or the amorphous form of Afatinib monomaleate of the present invention or the crystalline Form N or the amorphous form of Afatinib monomaleate prepared by preparation methods of the present invention, and at least one pharmaceutically acceptable excipient. Moreover, the pharmaceutical composition may also comprise other acceptable pharmaceutical salts, crystalline forms or amorphous forms of Afatinib. Optionally, the pharmaceutical composition may also comprise one or more other active pharmaceutical ingredient(s).

The excipients suitable for pharmaceutical composition are known to those skilled in the art and the selection of kinds, usage and amount are also known to those skilled in the art. For example, the excipients include sugars, cellulose and its derivatives, starch or modified starches, solid inorganics as calcium phosphate, calcium hydrogen phosphate, hydroxyl apatite, calcium sulphate or calcium carbonate, semisolids such as lipids or paraffin, the binders such as microcrystalline cellulose, ethylcellulose, carboxymethylcellulose, hydroxypropylmethylcellulose or hydroxyethylcellulose, glidants such as colloidal silica, light anhydrous silicic acid, crystalline cellulose, talc or magnesium stearate, disintegrants such as sodium starch glycolate, crospovidone, croscarmellose, sodium carboxymethylcellulose or dried corn starch, lubricants such as stearic acid, magnesium stearate, sodium stearylfumarate or polyethylene glycol.

Administration routes of the above pharmaceutical compositions include oral administration, intravenous injection and subcutaneous injection, injection into tissue, transdermal administration, rectal administration, nasal dripping, etc. Based on administration routes, certain dosage forms of the pharmaceutical compositions may be prepared, in solid forms or liquid forms. Oral solid dosage forms include tablet, granule, pulvis, pill and capsule, oral liquid dosage forms include solution, syrup, suspension, dispersion and emulsion, parental dosage forms include solution, dispersion or lyophilized dosage forms. The formulations may be suitable for immediate release, delayed release or controlled release of the active ingredient. The formulations may be a regular, dispersible, chewable, orally soluble or rapidly dissolving form. Preferably, the pharmaceutical composition is in a dosage form selected from the group consisting of tablet, capsule, granule, solution, syrup, suspension, dispersion, emulsion, pill and pulvis, more preferably, tablet, capsule, granule and pulvis.

The pharmaceutical compositions may be prepared by the method commonly known to those skilled in the art. In preparation of the pharmaceutical compositions, the crystalline Form N or the amorphous form of Afatinib monomaleate of the present invention is mixed with one or more pharmaceutically acceptable excipients, optionally with other pharmaceutically acceptable crystalline forms, amorphous forms or salts of Afatinib, optionally with one or more other active ingredients. Solid formulations may be prepared by direct mixing, granulation and other processes.

According to the objective of the present invention, the present invention provides use of the crystalline Form N or the amorphous form of Afatinib monomaleate of the present invention or the crystalline Form N or the amorphous form of Afatinib monomaleate prepared by preparation methods of the present invention in preparing drugs for treating terminal non-small cell lung cancer (NSCLC) or HER2 positive advanced breast cancer.

According to the objective of the present invention, the present invention provides a method for treating terminal non-small cell lung cancer (NSCLC) or HER2 positive advanced breast cancer, which comprises administrating to a patient in need of the treatment of a therapeutically effectively amount of the crystalline Form N or the amorphous form of Afatinib monomaleate of the present invention, the crystalline Form N or the amorphous form of Afatinib monomaleate prepared by preparation methods of the present invention or the above pharmaceutical composition containing the crystalline Form N or the amorphous form of Afatinib monomaleate of the present invention.

EXAMPLES

Figure 1:
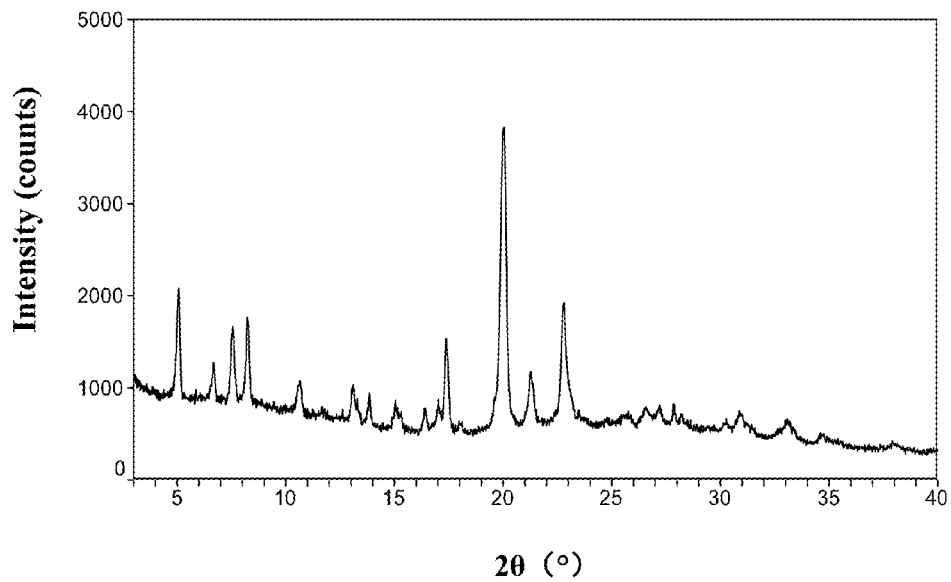
FIG. 1 is the XRPD pattern of the crystalline form of Afatinib dimaleate in the prior art.

The present invention refers further to the following examples. Those examples describe the preparations and applications of the solid forms of the present invention in detail. It will be apparent to those skilled in the art that various modifications can be made to materials and methods without departing from the scope of the present invention.

Instruments and Methods of the Characterization:

X-ray powder diffraction (XRPD) is performed on Bruker D8 Advance Diffractometer using a Cu-Kα X-radiation with the wavelength of 1.54 nm at 40 kV and 40 mA and equipped with θ-2θ goniometer, Mo monochrometer and Lynxeye detector. Before sample measurement, the instrument working condition is verified by the provided standard sample. The collection software is Diffrac Plus XRD Commander. The specimen is analyzed on a SiP non-reflective plate at room temperature. The specific test condition is as the following: 2θ scanning range is 3~40° with a step size of 0.02° and a speed of 0.2 s/step. Unless particularly specified, samples had not been grinded prior to the analysis.

Dynamic vapour sorption (DVS) data is collected using TA Instruments Q5000 TGA, the instrument control software is Thermal Advantage and the analytical software is Universal Analysis. Usually, 1-10 mg of the specimen is placed in a platinum pan, weight changes of the specimen are recorded by TA software within the process of the relative humidity change from 10% to 80% to 10%. Depending on specific situations, different sorption and desorption procedures may be used. An isothermal adsorption curve can be generated by the procession of software.

Polarizing microscope (PLM) image is collected using XP-500E polarizing microscope (Shanghai Changfang Optical Instrument Co., Ltd). Take some powder sample on a glass slide, drop some mineral oil to disperse the sample, cover a coverslip, then place the sample on the loading table of XP-500E polarizing microscope, observe morphology of the sample with appropriate magnification and take photos.

Proton nuclear magnetic resonance spectroscopy (1H-NMR) data is collected using Bruker Ascend Tm 500. Usually full-frequency excitation is used, with spectral width of 30 PPM, single pulse, 30° angle excitation, scanning of 16 times, digital orthogonal detection and a controlled temperature at 298K.

Hardness testing data is collected using hardness tester (Tianjin Xintianguang Optical Analytical Instrument Co., Ltd) and the model is YC-1. The operations are: place the test tablet on the test bench and locate it between the probe and the test bench, then slowly rotate the rotating disc counterclockwise and compress the force to the test tablet, when the test tablet is squeezed broken, the displayed value in the displaying window is the hardness of the test tablet.

High performance liquid chromatography (HPLC) data is collected using Agilent HPLC 1260. The instrument control software is B.04 online of Agilent ChemStation and the analytical software is B.04 offline of Agilent ChemStation. Using a C18, 150 mm×4.6 mm column, column temperature, 40° C., detection wavelength, 254 nm, flow rate, 0.3 ml/min, injection volume, 50 µl, running time, 30 min. Mobile phase A is water with 0.01% trifluoroacetate, mobile phase B is acetonitrile with 0.01% trifluoroacetate. The gradient is shown below:

| Gradient of mobile phase in HPLC | | |
|---|---|---|
| Time (min) | Mobile phase A (%) | Mobile phase B (%) |
| 0 | 95 | 5 |
| 3 | 95 | 5 |
| 10 | 5 | 95 |
| 15 | 5 | 95 |
| 30 | 5 | 95 |

Afatinib free base, as the starting material of the present invention, was prepared by the reference to the process in example 1 in patent document WO2002/50043A1.

If no specific descriptions were provided, the reagents used in the examples were purchased commercially.

The examples were operated at room temperature if no specific descriptions were provided.

Preparation Example 1

Crystalline form of Afatinib dimaleate in the prior art was prepared by the reference to the process described in example 3 in patent document CN1867564B. The operating procedures are detailed as follows:

1.0 g of Afatinib free base was dissolved in 14 mL of ethanol with stirring and heated to 70° C. 0.5 g of maleic acid was dissolved in 6 mL of ethanol with stirring. The ethanol solution of maleic acid was slowly added into the ethanol solution of Afatinib free base and stirred. After the solids were precipitated, the reaction solution was cooled to 20° C. and stirred for 2 hours, then stirred for 3 hours at 0° C., filtered, washed with ethanol, dried in a vacuum oven at 40° C. overnight, and Afatinib dimaleate was obtained in 90% yield.

Its X-ray powder diffraction pattern is shown in FIG. 1, showing that its crystalline form is the same as the crystalline form of Afatinib dimaleate in the prior art disclosed in patent document CN1867564B.

Figure 2:
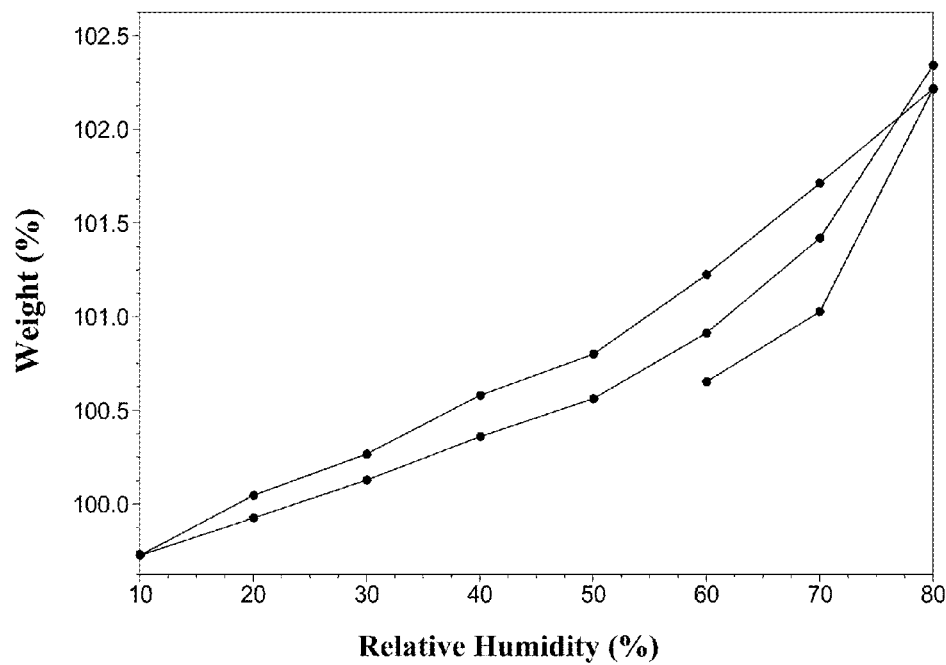
FIG. 2 is the isothermal adsorption curve of the crystalline form of Afatinib dimaleate in the prior art.

Its DVS isothermal adsorption curve is shown in FIG. 2, showing that weight change of the salt within the relative humidity range of 10%-80% is 2.6%.

Figure 3:
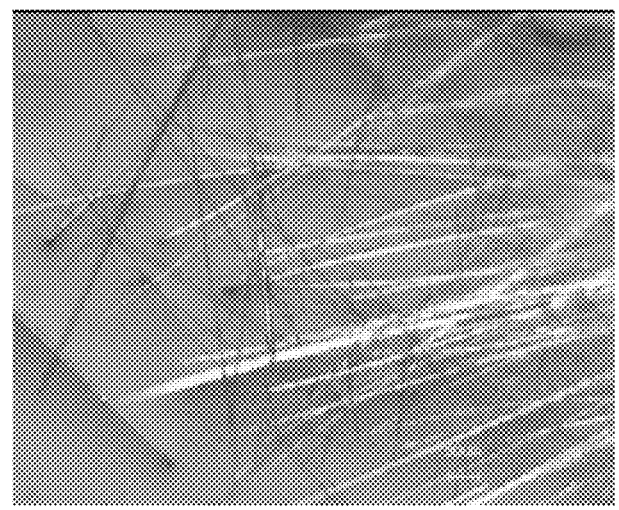
FIG. 3 is the PLM image of the crystalline form of Afatinib dimaleate in the prior art.

Its PLM image is shown in FIG. 3, displaying that the salts are fine needle-like crystals.

Example 1

The Preparation of Crystalline Form N of Afatinib Monomaleate

At room temperature, 5.0 g of Afatinib free base was dissolved in 20 mL of tetrahydrofuran by sonication, 1.79 g of maleic acid was added into the tetrahydrofuran solution of Afatinib free base, a solution was formed and was stirred, then 60 mL of methyl tert-butyl ether was slowly added to form a slurry, stirred for one day to crystallize, the precipitates were filtered and dried in vacuum oven at 40° C. for 8 hours, and 5.3 g of the crystalline Form N of Afatinib monomaleate was obtained in 85.6% yield.

The $^1$H-NMR (DMSO) data is shown below:

9.93 (s, 1H), 9.77 (s, 1H), 8.95 (s, 1H), 8.57 (s, 1H), 8.05-8.15 (m, 1H), 7.72-7.85 (m, 1H), 7.44 (t, J=9.0 Hz, 1H), 7.28 (s, 1H), 6.81 (s, 1H), 6.10 (s, 1H), 5.32 (s, 1H), 3.85-4.05 (m, 5H), 3.71-3.85 (m, 1H), 2.75-2.85 (m, 1H), 2.83 (s, 6H), 2.30-2.42 (m, 1H), 2.06-2.20 (m, 1H), showing that the ratio of Afatinib free base to maleic acid in the salt is about 1:1.

The HPLC determines that the content of Afatinib in the salt is 78.3%, which is close to the theoretical content (80.4%) of Afatinib in Afatinib monomaleate, indicating that the salt was formed from Afatinib and maleic acid in a molar ratio of 1:1.

Figure 4:
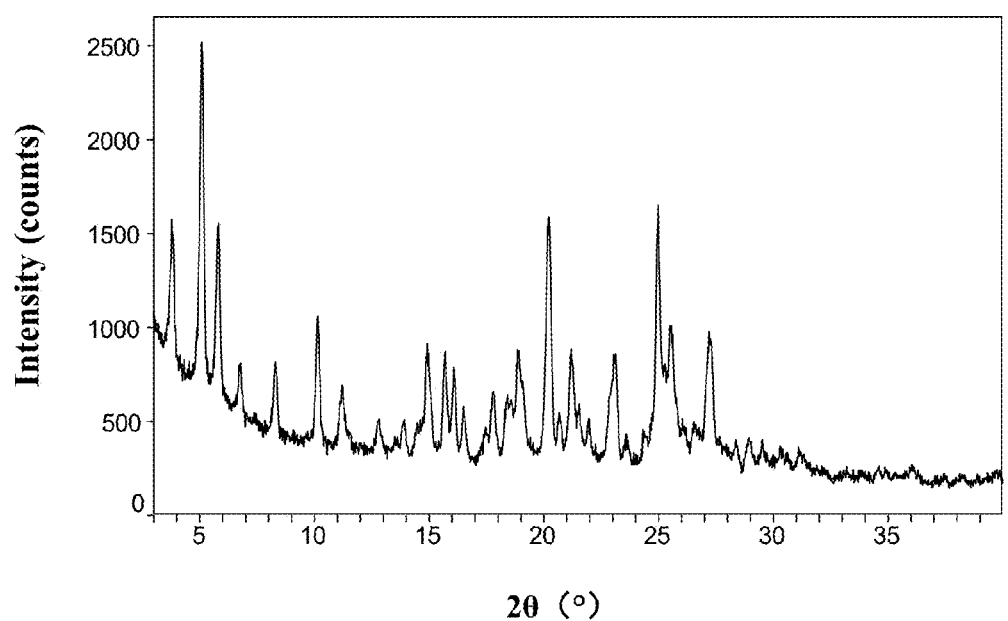
FIG. 4 is the XRPD pattern of the crystalline Form N of Afatinib monomaleate.

The XRPD pattern is shown in FIG. 4.

Figure 5:
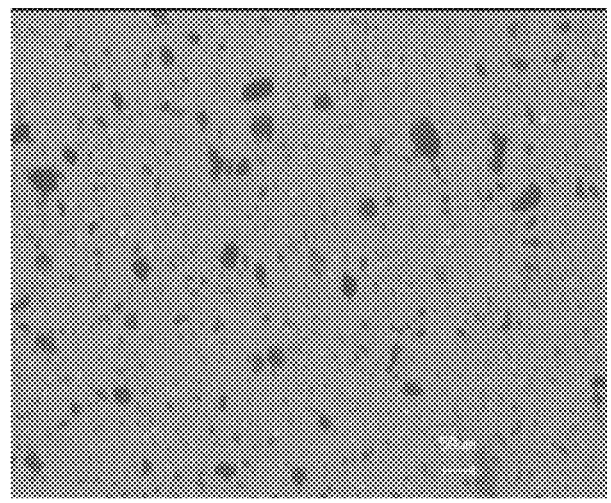
FIG. 5 is the PLM image of the crystalline Form N of Afatinib monomaleate.

The PLM image is shown in FIG. 5, showing fine granular crystals.

Figure 6:
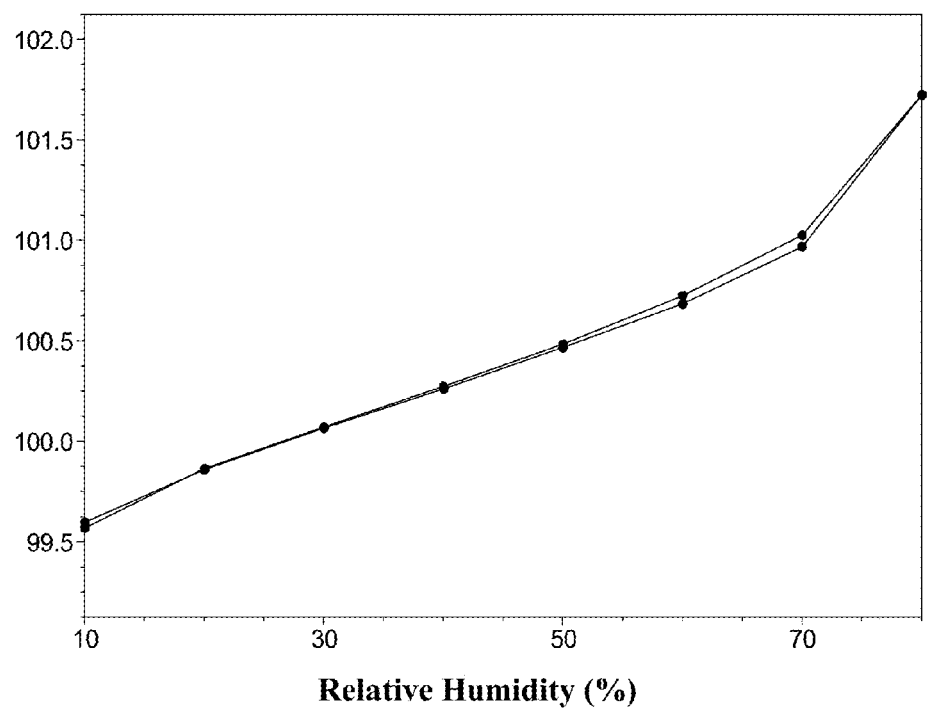
FIG. 6 is the isothermal adsorption curve of the crystalline Form N of Afatinib monomaleate.

The DVS isothermal adsorption curve is shown in FIG. 6, showing that weight change of the salt within the relative humidity range of 10%-80% is 2.1%.

Example 2

The Preparation of Crystalline Form N of Afatinib Monomaleate

At room temperature, 100 mg of Afatinib free base was dissolved in 0.5 mL of ethanol by sonication, 24 mg of maleic acid was added into the ethanol solution of Afatinib free base, a solution was formed and was stirred, then 2.5 mL of n-heptane was added and stirred for two days to crystallize, the precipitates were filtered and dried in a vacuum oven for 16 hours, and 105 mg of the crystalline Form N of Afatinib monomaleate was obtained in 84.7% yield.

Example 3

The Preparation of Crystalline Form N of Afatinib Monomaleate

At room temperature, 3.0 g of Afatinib free base was dissolved in 60 mL of isopropanol by sonication, 0.72 g of maleic acid was added into the isopropanol solution of Afatinib free base, a solution was formed and stirred, then 60 mL of isopropyl ether was slowly added to form a slurry, stirred for three days to crystallize, the precipitates were filtered and dried in a vacuum oven at 40° C. for 8 hours, and 3.2 g of the crystalline Form N of Afatinib monomaleate was obtained in 86.1% yield.

Example 4

The Preparation of Crystalline Form N of Afatinib Monomaleate

At room temperature, 0.5 g of Afatinib free base was dissolved in 5 mL of ethyl acetate by sonication, 0.12 g of maleic acid was added into the ethyl acetate solution of Afatinib free base, a solution was formed and stirred, then 20 mL of n-hexane was slowly added to form a slurry, stirred for two days to crystallize, the precipitates were filtered and dried in a vacuum oven at 40° C. for 8 hours, and 0.52 g of the crystalline Form N of Afatinib monomaleate was obtained in 83.9% yield.

Example 5

The Preparation of Crystalline Form N of Afatinib Monomaleate

At room temperature, 0.5 g of Afatinib free base was dissolved in 8 mL of isopropyl acetate by sonication, 0.12 g of maleic acid was added into the isopropyl acetate solution of Afatinib free base, a solution was formed and stirred, then 24 mL of diethyl ether was slowly added to form a slurry, stirred for two days to crystallize, the precipitates were filtered and dried in vacuum oven at 40° C. for 8 hours, and 0.44 g of the crystalline Form N of Afatinib monomaleate was obtained in 71% yield.

Example 6

The Preparation of Crystalline Form N of Afatinib Monomaleate

At room temperature, 1.0 g of Afatinib free base was dissolved in 4 mL of 1,4-dioxane by sonication, 0.24 g of maleic acid was added into the 1,4-dioxane solution of Afatinib free base, a solution was formed and stirred, then 4 mL of n-octane was slowly added to form a slurry, stirred for one day to crystallize, the precipitates were filtered and dried in a vacuum oven at 40° C. for 8 hours, and 0.92 g of the crystalline Form N of Afatinib monomaleate was obtained in 74.3% yield.

Example 7

The Preparation of Crystalline Form N of Afatinib Monomaleate

At room temperature, 0.5 g of Afatinib free base was dissolved in 5 mL of 1,3-dioxolane by sonication, 0.12 g of maleic acid was added into the 1,3-dioxolane solution of Afatinib free base, a solution was formed and stirred, then 5 mL of propyl ether was slowly added to form a slurry, stirred for one day to crystallize, the precipitates were filtered and dried in a vacuum oven at 40° C. for 8 hours, and 0.39 g of the crystalline Form N of Afatinib monomaleate was obtained in 63.0% yield.

The $^1$H-NMR data, HPLC chromatograms, XRPD patterns, PLM images and DVS isothermal adsorption curves of the samples prepared in examples 2~7 were similar to those of the sample prepared in example 1, indicating that the crystalline forms obtained in examples 2~7 were the same as that of example 1.

Example 8

The Preparation of the Amorphous Form of Afatinib Monomaleate 500 mg of Afatinib free base was dissolved in 10 mL of methanol by sonication, 120 mg of maleic acid was added into the methanol solution of Afatinib free base, a solution was formed, stirred, and concentrated to dry under reduced pressure, and 610 mg of the solid was obtained. The solid was confirmed by the $^1$H-NMR to be Afatinib monomaleate, and the yield is 98.5%.

Figure 7:
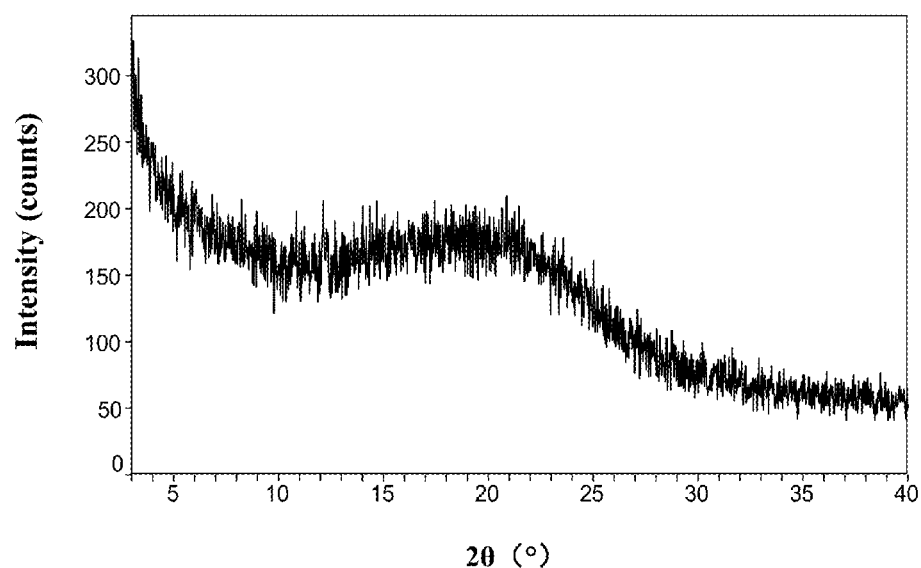
FIG. 7 is the XRPD pattern of the amorphous form of Afatinib monomaleate.

The XRPD pattern is shown in FIG. 7, indicating that the solid is an amorphous form.

Example 9

According to tablet formulas of Table 1, tablets A, B, C, D and E were prepared with different dosages containing the crystalline Form N or the amorphous form of Afatinib monomaleate of the present invention.

TABLE 1

Tablet Formulas

| Ingredients | Weight percentage (%/tablet) | A Dosage (mg/table) | B Dosage (mg/table) | C Dosage (mg/table) | D Dosage (mg/table) | E Dosage (mg/table) |
|---|---|---|---|---|---|---|
| the crystalline Form N or the amorphous form of Afatinib monomaleate | 13.63 | 24.78 | 37.16 | 49.55 | 61.94 | 86.72 |
| Afatinib free base (equivalent to crystalline Form N or the amorphous form of Afatinib monomaleate) | 11 | 20 | 30 | 40 | 50 | 70 |
| Lactose monohydrate | 71.60 | 128.64 | 192.97 | 257.29 | 321.61 | 450.25 |
| Microcrystalline cellulose | 10.27 | 18.48 | 27.72 | 36.96 | 46.20 | 64.68 |
| Crospovidone | 2.00 | 3.6 | 5.4 | 7.2 | 9.0 | 12.6 |
| Anhydrous colloidal silica | 0.50 | 0.90 | 1.35 | 1.80 | 2.25 | 3.15 |
| Magnesium stearate | 2.00 | 3.6 | 5.4 | 7.2 | 9.0 | 12.6 |
| Total | 100 | 180 | 270 | 360 | 450 | 630 |

The tablets are prepared by the following procedures: pass microcrystalline cellulose, crospovidone, the unmilled crystalline form N or amorphous form of Afatinib monomaleate through a 30-mesh sieve (about 430 μm to 655 μm). Load crospovidone into a bivalve tumble mixer with three cubic feet, add microcrystalline cellulose and lactose monohydrate, mix for five minutes, then add the crystalline Form N or the amorphous form of Afatinib monomaleate of the present invention, mix for twenty-five minutes. Pass the premix through a roller compactor with a hammer mill at the discharge point and bring it back to the tumble mixer. Add magnesium stearate and anhydrous colloidal silica into the tumble mixer, mix for about three minutes. Press the final mixture on the rotary tablet press and the batch is 200,000 tablets.

Example 10

According to single dosage formula and batch formula of capsules in table 2, the capsules containing the crystalline Form N or the amorphous form of Afatinib monomaleate of the present invention were prepared.

TABLE 2

Capsule Formulas

| Ingredients | Weight percent (%/capsule) | Single dosage (mg/capsule) | Batch (kg/batch) |
|---|---|---|---|
| the crystalline Form N or the amorphous form of Afatinib monomaleate | 14.87 | 74.33 | 6.24 |
| Lactose monohydrate | 72.54 | 362.72 | 30.47 |
| Microcrystalline cellulose | 10.53 | 52.65 | 4.42 |
| Magnesium stearate | 2.06 | 10.3 | 0.87 |
| Total | 100.0 | 500 | 42.00 |

The capsules are prepared by the following procedures: passlactose monohydrate, microcrystalline cellulose and the crystalline Form N or the amorphous form of Afatinib monomaleate through a 710 μm sieve, load into a diffusion mixer with baffles insert and mix for fifteen minutes. Pass magnesium stearate through a 210 μm sieve, add it into the diffusion mixer, and then fill the mixture into number 0# capsules using Dosator-capsule filling machine. The weight of obtained capsule is 500 mg per capsule and the batch is 84000 capsules.

Comparative Example 1

Take 5 mg of the crystalline form of Afatinib dimaleate in the prior art prepared in preparation example 1 and the crystalline Form N of Afatinib monomaleate prepared in example 1 as the sample respectively, pure water was added into each sample progressively at 25° C. until the sample completely dissolved, then calculate the solubility of the sample according to the weight of the sample and water. The results are shown in Table 3.

TABLE 3

Results of the solubility

| Crystalline forms of Afatinib salts | solubility (mg/mL) |
|---|---|
| The crystalline form of Afatinib dimaleate salt in the prior art | 7.5 |
| The crystalline Form N of Afatinib monomaleate | 126.9 |

The results of the solubility in Table 3 show that the solubility of the crystalline Form N of Afatinib monomaleate of the present invention is significantly higher than that of the crystalline form of Afatinib dimaleate in the prior art, indicating that the crystalline Form N of Afatinib monomaleate has better solubility at room temperature.

Comparative Example 2

According to the tablet formula C and its preparation process described in example 9, prepare 100 tablets containing the crystalline form of Afatinib dimaleate in the prior art or containing the crystalline Form N of Afatinib monomaleate of the present invention respectively. Observe the tableting processes and tablet shapes.

The result shows that during the tableting process, the tablets containing the crystalline form of Afatinib dimaleate in the prior art have obvious sticking phenomenon and the tablets containing the crystalline Form N of Afatinib monomaleate of the present invention have no sticking phenomenon. The result indicates that in terms of processibility of the tablets, granular crystal morphology of the crystalline Form N of Afatinib monomaleate of the present invention is superior to fine needle morphology of the crystalline form of Afatinib dimaleate in the prior art.

Comparative Example 3

Take 20 intact tablets containing the crystalline form of Afatinib dimaleate in the prior art and 20 intact tablets containing the crystalline Form N of Afatinib monomaleate of the present invention prepared in comparative example 2, and test their hardness.

The result shows that the average hardness of tablets containing the crystalline Form N of Afatinib monomaleate is higher than that of tablets containing the crystalline form of Afatinib dimaleate in the prior art. The result indicates that in terms of tablet compressibility, granular crystal morphology of the crystalline Form N of Afatinib monomaleate of the present invention is superior to fine needle morphology of the crystalline form of Afatinib dimaleate in the prior art.

The described above are only specific embodiments of the present invention, but not limitations to the scope of the present invention. Any changes or replacements without creative work, which made by those skilled in the art within the technical scope disclosed by the present invention, should be fallen within the scope of the present invention.

What is claimed is:

1. Crystalline Form N of Afatinib monomaleate with the structural formula shown below,

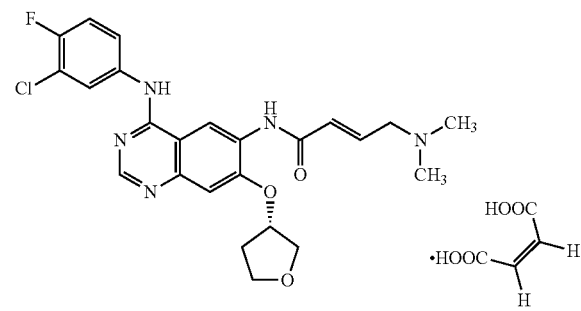

wherein, measured using Cu-Kα radiation, the X-ray powder diffraction pattern of the crystalline Form N of Afatinib monomaleate, expressed as 2θ angles, has the following characteristic peaks: 3.8±0.2°, 5.1±0.2°, 5.8±0.2°, 10.1±0.2°, 14.9±0.2° and 20.2±0.2°.

2. The crystalline Form N of Afatinib monomaleate according to claim 1, wherein the X-ray powder diffraction pattern of the crystalline Form N of Afatinib monomaleate, expressed as 2θ angles, has the following characteristic peaks: 3.8±0.2°, 5.1±0.2°, 5.8±0.2°, 6.8±0.2°, 8.3±0.2°, 10.1±0.2°, 11.2±0.2°, 14.9±0.2°, 15.7±0.2°, 18.9±0.2°, 20.2±0.2° and 25.0±0.2°.

3. The crystalline Form N of Afatinib monomaleate according to claim 2, wherein the X-ray powder diffraction pattern of the crystalline Form N of Afatinib monomaleate, expressed as 2θ angles, has the following characteristic peaks with their relative intensities:

| Diffraction angel 2θ | Relative intensity % |
| --- | --- |
| 3.8 ± 0.2° | 39.7 |
| 5.1 ± 0.2° | 100.0 |
| 5.8 ± 0.2° | 48.9 |
| 6.8 ± 0.2° | 14.6 |
| 8.3 ± 0.2° | 21.0 |
| 10.1 ± 0.2° | 36.8 |
| 11.2 ± 0.2° | 17.7 |
| 14.9 ± 0.2° | 30.8 |
| 15.7 ± 0.2° | 28.5 |
| 16.1 ± 0.2° | 24.8 |
| 16.5 ± 0.2° | 12.8 |
| 17.8 ± 0.2° | 18.4 |
| 18.9 ± 0.2° | 29.3 |
| 20.2 ± 0.2° | 67.4 |
| 21.2 ± 0.2° | 28.5 |
| 23.1 ± 0.2° | 30.9 |
| 25.0 ± 0.2° | 71.4 |
| 25.5 ± 0.2° | 34.7 |
| 27.2 ± 0.2° | 35.1. |

4. Crystalline Form N of Afatinib monomaleate with the structural formula shown below,

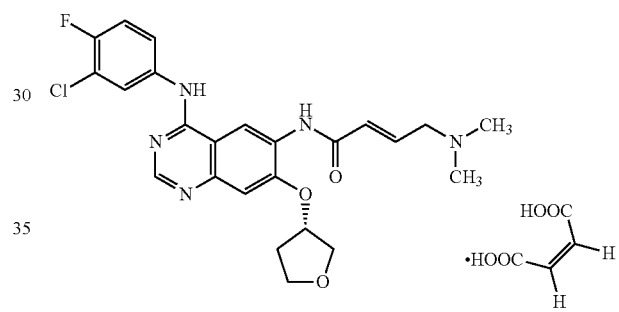

Wherein, measured using Cu-Kα radiation, the X-ray powder diffraction pattern of the crystalline Form N of Afatinib monomaleate has the characteristic peaks as depicted in FIG. 4.

5. A method for preparing crystalline Form N of Afatinib monomaleate according to claim 1 comprising:

dissolving Afatinib free base in a solvent selected from the group consisting of tetrahydrofuran, ethanol, isopropanol, ethyl acetate, isopropyl acetate, 1,4-dioxane and 1,3-dioxolane;

adding under stirring, from 1 to 1.5 times molar amount of maleic acid to the solution;

slowly adding an anti-solvent to form a slurry, wherein, the anti-solvent is selected from the group consisting of methyl tert-butyl ether, n-heptane, isopropyl ether, n-hexane, diethyl ether, n-octane and propyl ether, and, wherein, the ratio of the solvent to the anti-solvent is from 1:1 to 1:5;

continuing stirring for 1 to 3 days to crystallize;

filtering the precipitates; and drying the precipitates to obtain the crystalline Form N of Afatinib monomaleate.

6. An amorphous form of Afatinib monomaleate with the structural formula shown below

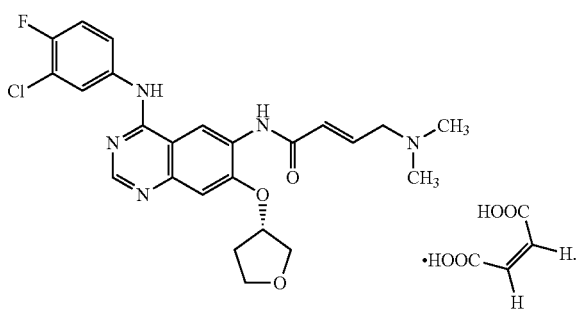

wherein, measured using Cu-Kα radiation, the X-ray powder diffraction pattern of the amorphous form of Afatinib monomaleate has the characteristic amorphous halo in the XRPD pattern as depicted in FIG. 7.

7. A method for preparing amorphous form of Afatinib monomaleate according to claim 6 comprising:
dissolving Afatinib free base in methanol;
adding under stirring, from 1 to 1.5 times molar amount of maleic acid to the solution; and
concentrating the solution to obtain the amorphous form of Afatinib monomaleate.

8. A pharmaceutical composition, comprising an amount of the crystalline Form N of Afatinib monomaleate according to claim 1, and at least one pharmaceutical acceptable excipient.

9. The pharmaceutical composition according to claim 8, wherein the pharmaceutical composition is in a dosage form selected from the group consisting of tablet, capsule, granule, solution, syrup, suspension, dispersion, emulsion, pill and pulvis.

10. A pharmaceutical composition, comprising a therapeutically effective amount of the crystalline Form N of Afatinib monomaleate prepared according to claim 5, and at least one pharmaceutical acceptable excipient.

11. The pharmaceutical composition according to claim 10, wherein the pharmaceutical composition is in a dosage form selected from the group consisting of tablet, capsule, granule, solution, syrup, suspension, dispersion, emulsion, pill and pulvis.

12. A pharmaceutical composition, comprising an amount of the amorphous form of Afatinib monomaleate according to claim 6, and at least one pharmaceutical acceptable excipient.

* * * * *